US00PP27678P2

(12) United States Plant Patent
Dummen

(10) Patent No.: US PP27,678 P2
(45) Date of Patent: Feb. 14, 2017

(54) ***LOBELIA* PLANT NAMED 'DUELOBELCIE15'**

(50) Latin Name: *Lobelia hybrida*
Varietal Denomination: Duelobelcie15

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/756,083

(22) Filed: Jul. 29, 2015

(51) Int. Cl.
*A01H 5/02* (2006.01)

(52) U.S. Cl.
USPC ..... Plt./451

(58) Field of Classification Search
USPC ..... Plt./451
See application file for complete search history.

*Primary Examiner* — Susan McCormick Ewoldt
(74) *Attorney, Agent, or Firm* — C. A. Whealy

(57) ABSTRACT

A new and distinct cultivar of *Lobelia* plant named 'Duelobelcie15', characterized by its compact, upright to outwardly spreading and semi-mounding plant habit; moderately vigorous growth habit; freely branching habit; early and freely flowering habit; and light blue-colored flowers.

1 Drawing Sheet

Botanical designation: *Lobelia hybrida.*
Cultivar denomination: 'DUELOBELCIE15'.

BACKGROUND OF THE INVENTION

The present invention relates to a new and distinct cultivar of *Lobelia* plant, botanically known as *Lobelia hybrida* and hereinafter referred to by the name 'Duelobelcie15'.

The new *Lobelia* plant is a product of a planned breeding program conducted by the Inventor in Rheinberg, Germany. The objective of the breeding program is to create new compact *Lobelia* plants with good vigor and numerous attractive flowers.

The new *Lobelia* plant originated from a cross-pollination made by the Inventor in June, 2012 of a proprietary selection of *Lobelia hybrida* identified as code number F10-1308-001, not patented, as the female, or seed, parent with a proprietary selection of *Lobelia hybrida* identified as code number F12-1204-005, not patented, as the male, or pollen, parent. The new *Lobelia* plant was discovered and selected by the Inventor as a single flowering plant from within the progeny of the stated cross-pollination grown in a controlled greenhouse environment in Rheinberg, Germany in May, 2014.

Asexual reproduction of the *Lobelia* plant by vegetative cuttings in Rheinberg, Germany since June, 2014 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duelobelcie15'. These characteristics in combination distinguish 'Duelobelcie15' as a new and distinct *Lobelia* plant:

1. Compact, upright to outwardly spreading and semi-mounding plant habit.
2. Moderately vigorous growth habit.
3. Freely branching habit.
4. Early and freely flowering habit.
5. Light blue-colored flowers.

Plants of the new *Lobelia* differ primarily from plants of the female parent selection in the following characteristics:

1. Plants of the new *Lobelia* are more compact than plants of the female parent selection.
2. Plants of the new *Lobelia* and the female parent selection differ in flower color as plants of the female parent selection have lavender-colored flowers.

Plants of the new *Lobelia* differ primarily from plants of the male parent selection in flower color as plants of the male parent selection have darker blue-colored flowers.

Plants of the new *Lobelia* can be compared to plants of *Lobelia* 'Hot Water Blue Improved', not patented. In side-by-side comparisons conducted in Rheinberg, Germany, plants of the new *Lobelia* differed from plants of 'Hot Water Blue Improved' in the following characteristics:

1. Plants of the new *Lobelia* were more compact than plants of 'Hot Water Blue Improved'.
2. Plants of the new *Lobelia* and 'Hot Water Blue Improved' differed in flower color as plants of 'Hot Water Blue Improved' had darker blue-colored flowers.

BRIEF DESCRIPTION OF THE PHOTOGRAPH

The accompanying colored photograph illustrates the overall appearance of the new *Lobelia* plant showing the colors as true as it is reasonably possible to obtain in colored reproductions of this type. Colors in the photograph may differ slightly from the color values cited in the detailed botanical description which accurately describe the actual colors of the new *Lobelia* plant.

The photograph comprises a side perspective view of a typical flowering plant of 'Duelobelcie15' grown in a container.

DETAILED BOTANICAL DESCRIPTION

The aforementioned photograph and following observations, measurements and values describe plants grown in 10.5-cm containers during the summer in a glass-covered greenhouse in Rheinberg, Germany and under cultural practices typical of commercial *Lobelia* production. During the production of the plants, day and night temperatures averaged 18° C. and light levels averaged 4,500 lux. Plants were pinched one time three weeks after planting and were 20 weeks old when the photograph and the description were taken. In the description, color references are made to The Royal Horticultural Society Colour Chart, 2011 Edition, except where general terms of ordinary dictionary significance are used.

Botanical classification: *Lobelia hybrida* 'Duelobelcie15'.

Parentage:

*Female parent*.—Proprietary selection of *Lobelia hybrida* identified as code number F10-1308-001, not patented.

*Male parent*.—Proprietary selection of *Lobelia hybrida* identified as code number F12-1204-005, not patented.

Propagation:

*Type*.—Terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Form*.—Compact, upright to outwardly spreading and semi-mounding plant habit; freely branching habit with about 23 lateral branches per plant each primary lateral developing multiple secondary laterals; moderately vigorous growth habit; rapid growth rate.

*Plant height*.—About 23 cm.

*Plant width*.—About 51 cm.

*Lateral branch description*.—Length: About 23 cm to 27 cm. Diameter: About 2 mm. Internode length: About 1.5 cm to 3 cm. Strength: Strong, flexible. Texture: Pubescent. Color: Close to 146A.

Leaf description:

*Arrangement*.—Alternate, simple.

*Length*.—About 1.7 cm.

*Width*.—About 8 mm.

*Shape*.—Elliptical to oblanceolate.

*Apex*.—Acute; recurved.

*Base*.—Attenuate.

*Margin*.—Entire or with shallow and irregular serrations.

*Texture, upper and lower surfaces*.—Pubescent.

*Luster, upper and lower surfaces*.—Matte.

*Venation pattern*.—Pinnate; arcuate.

*Color*.—Developing leaves, upper surface: Close to 143A. Developing leaves, lower surface: Close to 143B. Fully expanded leaves, upper surface: Close to 147A; venation, close to 147A. Fully expanded leaves, lower surface: Close to 146B and 178A; venation, close to 147A.

*Petioles*.—Length: About 3 mm to 5 mm. Diameter: About 2 mm to 3 mm. Texture, upper and lower surfaces: Smooth, glabrous. Color, upper surface: Close to 143A. Color, lower surface: Close to 143C.

Flower description:

*Flower arrangement, form and habit*.—Solitary axillary flowers with three broad lower (two laterals and one lip) petals and two narrower upper (banner) petals; petals fused towards the base into a narrow tube; freely flowering habit with about 24 to 36 flowers and flower buds per lateral stem at one time and about 550 to 800 flowers developing per plant over the flowering season; flowers face upright to outwardly.

*Natural flowering season*.—Early flowering habit, plants begin flowering about seven weeks after planting; in the garden, plants flower continuously from the spring until frost in Germany.

*Flower longevity on the plant*.—Longevity of individual flowers is highly dependent on environmental conditions; flowers typically last about four to five days on the plant; flowers persistent.

*Fragrance*.—None detected.

*Flower buds*.—Length: About 1 cm. Diameter: About 2.8 mm. Shape: Obovate. Texture: Pubescent. Color: Close to 145C and 96C.

*Flower diameter*.—About 1.9 cm.

*Flower depth (height)*.—About 2.1 cm.

*Flower throat diameter*.—About 2 mm to 3 mm.

*Flower tube length*.—About 6 mm to 8 mm.

*Flower tube diameter at base*.—About 2.5 mm to 4 mm.

*Petals*.—Arrangement: Single whorl of five petals, petals fused at the base into a narrow tube; three broad lower (two laterals and one lip) petals and two narrower upper (banner) petals. Three lower petals: Lobe length: About 10.2 mm. Lobe width: About 6.6 mm. Shape: Obovate. Apex: Rounded. Margin: Entire. Texture, upper and lower surfaces: Smooth, glabrous; velvety. Two upper petals: Lobe length: About 7.2 mm. Lobe width: About 1.5 mm to 3 mm. Shape: Lanceolate. Apex: Rounded. Margin: Entire. Texture, upper and lower surfaces: Smooth, glabrous; velvety. Color, all petals: When opening, upper surface: Close to 96C; towards the base, close to N155D; spots, close to 99B. When opening, lower surface: Close to 96D and 97C. Fully opened, upper surface: Close to 98C; towards the base, close to N155D; spots, close to 95B; venation, close to 98C; color becoming closer to 95D with development. Fully opened, lower surface: Close to 97B to 97D; venation, close to 97C. Throat: Close to 97A to 97D; venation, close to 97B. Tube: Close to 97C; venation, close to 97B.

*Sepals*.—Arrangement: Single whorl of five sepals, fused at the base; star-shaped calyx. Length: About 5 mm to 6 mm. Width: About 1 mm. Shape: Lanceolate. Apex: Acuminate. Margin: Entire. Texture, upper and lower surfaces: Pubescent. Color, upper surface: Close to 146A. Color, lower surface: Close to 146B.

*Peduncles*.—Length: About 1.6 cm. Diameter: About 1 mm. Aspect: About 45° from the lateral stem axis. Strength: Moderately strong, flexible. Texture: Pubescent. Color: Close to 146B.

*Reproductive organs*.—Stamens: Quantity per flower: About five. Filament length: About 6 mm to 7 mm. Filament color: Close to 95D and 97A. Anther length: About 2 mm. Anther shape: Lanceolate. Anther color: Close to 201A. Pollen amount: Scarce. Pollen color: Close to 155D. Pistils: Quantity per flower: One. Pistil length: About 7 mm to 9 mm. Stigma shape: Round. Stigma color: Close to 92B. Style length: About 5 mm to 7 mm. Style color: Close to 144C. Ovary color: Close to 144A.

*Seeds and fruits*.—Seed and fruit development have not been observed on plants of the new *Lobelia*.

Disease & pest resistance: Plants of the new *Lobelia* have not been noted to be resistant to pathogens and pests common to *Lobelia* plants.

Temperature tolerance: Plants of the new *Lobelia* have been observed to tolerate temperatures from about 5° C. to about 40° C.

It is claimed:

1. A new and distinct *Lobelia* plant named 'Duelobelcie15' as illustrated and described.

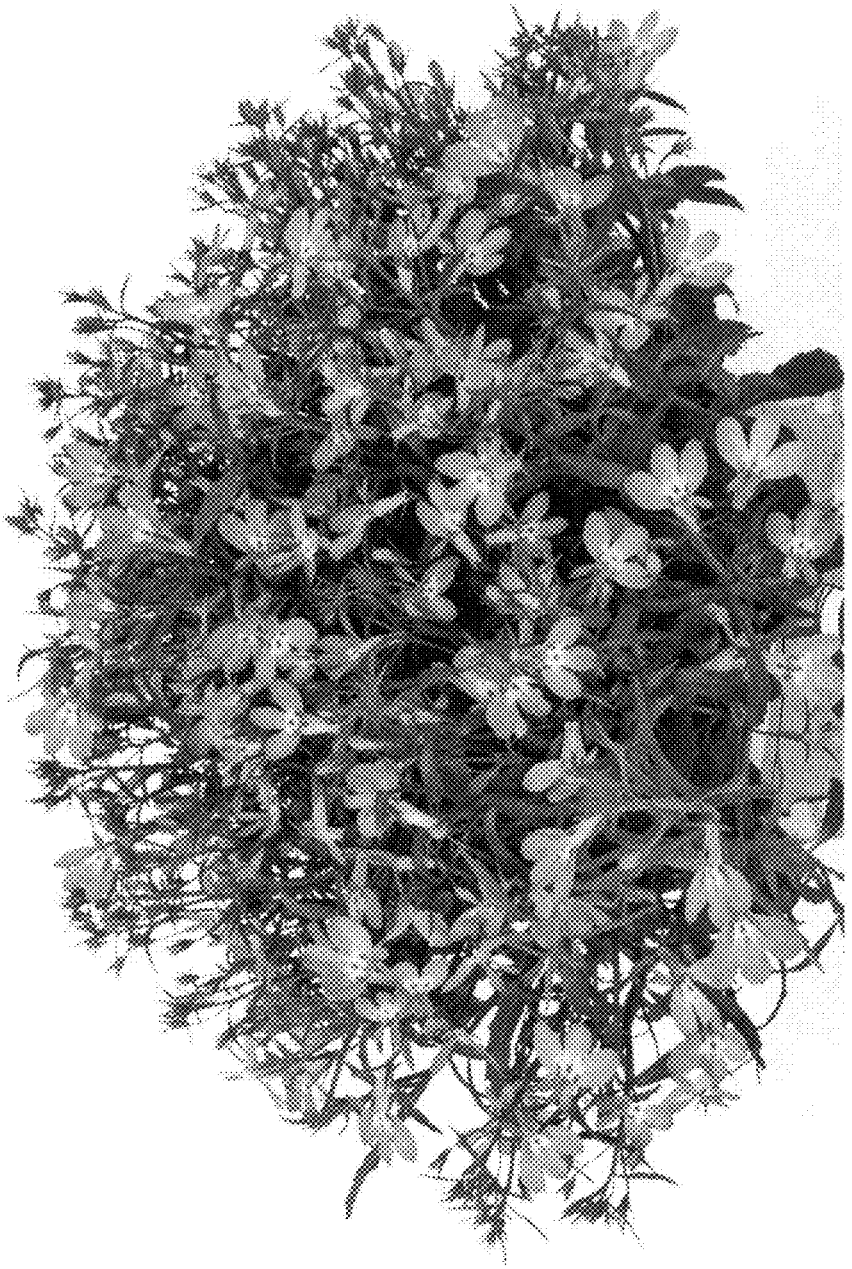

* * * * *